United States Patent [19]

Shen et al.

[11] Patent Number: 5,936,092

[45] Date of Patent: *Aug. 10, 1999

[54] METHODS AND COMPOSITIONS FOR LIPIDIZATION OF HYDROPHILIC MOLECULES

[75] Inventors: Wei-Chiang Shen, San Marino; Hossein M. Ekrami, Los Angeles, both of Calif.

[73] Assignee: The University of Southern California, Los Angeles, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/742,357

[22] Filed: Nov. 1, 1996

Related U.S. Application Data

[60] Division of application No. 08/524,362, Sep. 5, 1995, which is a continuation-in-part of application No. 08/349,717, Jan. 25, 1995, abandoned.

[51] Int. Cl.[6] .......................... C07C 321/28; C07J 41/00; C07D 213/64; C07D 213/70

[52] U.S. Cl. .......................... 546/294; 552/544; 552/548; 562/431

[58] Field of Search .......................... 546/294; 562/431; 552/544, 548

[56] References Cited

U.S. PATENT DOCUMENTS

| 5,599,903 | 2/1997 | Kauvar et al. .......................... 530/331 |
| 5,679,643 | 10/1997 | Kauvar et al. .......................... 514/18 |
| 5,763,570 | 6/1998 | Kauvar et al. .......................... 530/331 |

FOREIGN PATENT DOCUMENTS

| 0 482 766 | 4/1992 | European Pat. Off. . |
| WO 91/16067 | 10/1991 | WIPO . |

OTHER PUBLICATIONS

K.Brocklehurst,Journal of Biochemistry,vol. 133(3),pp. 573–584, Mar. 1973.

Chemical Abstracts,vol. 73,(11),abst.No.56,440t,Sep.14, 1970.

Chemical Abstracts,vol. 74,(11),abst.No.54,179m,Mar. 15, 1971.

Chemical Abstracts,vol 73,(25).abst.No. 175,175y(Dec. 21, 1970.

Müller, C.E. et al., "Lipophilic disulfide prodrugs—syntheses and disulfide bond cleavage," *International J. Pharmaceutics* 57:41–47 (1989).

Huang, W. et al., "Lipophilic Multiple Antigen Peptide System For Peptide Immunogen and Synthetic Vaccine," *Mol. Immunol.* 31:1191–1199 (Oct. 1994).

Ubuka, T. et al., "Synthesis of disulfides related to glutathione and their detection in tissue," *Ganryu Aminosan* 8(*1*):153–157 (1985).

Ubuka, T. et al., "Synthesis of disulfides related to glutathione and their detection in tissue," *Chem. Abstracts* 106:728, Abstract No. 156843v (1987).

Patent Abstract of Japanese Publication No. 63246382.

*Primary Examiner*—Alan L. Rotman
*Attorney, Agent, or Firm*—Sterne, Kessler, Goldstein & Fox P.L.L.C.

[57] ABSTRACT

Fatty acid derivatives of sulfhydryl-containing compounds (for example, sulfhydryl-containing peptides or proteins) comprising fatty acid-conjugated products with a disulfide linkage are employed for delivery of the compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties.

9 Claims, 8 Drawing Sheets

METHODS AND COMPOSITIONS FOR LIPIDIZATION OF HYDROPHILIC MOLECULES

This application is a division of application Ser. No. 08/524,362 filed on Sep. 5, 1995 which application is now pending, and which is a continuation-in-part of application Ser. No. 08/349,717 filed Jan. 25, 1995, which application is now abandoned.

BACKGROUND OF THE INVENTION

The present invention relates generally to the fields of biology and medicine. More particularly, the present invention is directed to methods and compositions useful in increasing in mammals the absorption and retention of hydrophilic molecules, in particular peptides and proteins.

Advances in biotechnology have made possible the production of large amounts of therapeutically active and pure proteins and peptides. Currently, the therapeutic effects of most of these agents can be achieved only when they administered via invasive routes, such as by injection. Since most proteins have very short half lives, effective concentrations of these agents can be maintained only when administered by frequent injections.

Although the administration of proteins by injection is the most effective means of their delivery in vivo, patient tolerance of multiple injections is very poor. In addition, the administration of drugs via the injection routes is a skilled job and requires training; this skill and training may not always be transferable to patients. In cases where protein drugs have a life-saving role, the administration by the injection route can be accepted by the patients. However, in cases where protein drugs are just one of several possible therapies, injections of proteins and peptides are unlikely to be accepted by the patients. Therefore, alternative routes of protein and peptide delivery need to be developed.

Alternative routes of protein and peptide delivery may include the buccal, nasal, oral, pulmonary, rectal and ocular routes. Without exception, these routes are less effective than the parenteral routes of administration. However, these routes of protein and peptide delivery are still far more attractive than the parenteral routes because they offer convenience and control to the patients. The oral route is particularly attractive because it is the most convenient and patient-compliant.

Mucosal barriers, which separate the inside of the body from the outside (e.g. GI, ocular, pulmonary, rectal and nasal mucosa), comprise a layer of tightly joined cell monolayers which strictly regulates the transport of molecules. Individual cells in barriers are joined by tight junctions which regulate entry into the intercellular space.

Hence, the mucosa is at the first level a physical barrier, transport through which depends on either the transcellular or the paracellular pathways [Lee, V. H. L. (1988) CRC Critical Rev. Ther. Drug Delivery Sys. 5, 69–97].

Paracellular transport through water filled tight junctions is restricted to small molecules (MW<1 kDa) and is essentially a diffusion process driven by a concentration gradient across the mucosa [Lee (1988), supra; Artursson, P., and Magnusson, C. (1990) J. Pharm. Sci. 79, 595–600]. The tight junctions comprise less than 0.5% of the total surface area of the mucosa [Gonzalez-Mariscal, L. M. et al. (1985) J. Membrane. Biol. 86, 113–125; Vetvicka, V., and Lubor, F. (1988) CRC Critical Rev. Ther. Drug Deliv. Sys. 5, 141–170]; therefore, they play only a minor role in the transport of protein drugs across the mucosa.

The transcellular transport of small drugs occurs efficiently provided the physiochemical properties of the drug are suited to transport across hydrophobic cell barriers. However, the transcellular transport of proteins and peptides is restricted to the process of transcytosis [Shen, W. C. et al. (1992) Adv. Drug Delivery Rev. 8, 93–113]. Transcytosis is a complex process in which proteins and peptides are taken up into vesicles from one side of a cell, and are subsequently shuttled through the cell to other side of the cell, where they are discharged from the endocytic vesicles [Mostov, K. E., and Semister, N. E. (1985) Cell 43, 389–390]. The cell membrane of mucosal barriers is a hydrophobic lipid bilayer which has no affinity for hydrophilic, charged macromolecules like proteins and peptides. In addition, mucosal cells may secrete mucin which can act as a barrier to the transport of many macromolecules [Edwards, P. (1978) British Med. Bull. 34, 55–56]. Therefore, unless specific transport mechanisms exist for protein and peptide, their inherent transport across mucosal barriers is almost negligible.

In addition to providing a tight physical barrier to the transport of proteins and peptides, mucosal barriers possess enzymes which can degrade proteins and peptides before, after, and during their passage across the mucosa. This barrier is referred to as the enzymatic barrier. The enzymatic barrier consists of endo- and exopeptidase enzymes which cleave proteins and peptides at their terminals or within their structure. Enzymatic activity of several mucosa have been studied and the results demonstrated that substantial protease activity exists in the homogenates of buccal, nasal, rectal and vaginal mucosa of albino rabbits and that these activities are comparable to those present in the ilium [Lee et al. (1988), supra]. Therefore, regardless of the mucosa being considered, the enzymatic barrier present will feature strongly in the degradation of the protein and peptide molecules.

The N and the C termini of peptides are charged and the presence of charged side chains impart highly hydrophilic characteristics on these macromolecules. In addition, the presence of charged side chains means that proteins and peptides have strong hydrogen binding capacities; this H-binding capacity has been demonstrated to play a major role in inhibiting the transport of even small peptides across cell membranes [Conradi, R. A. et al. (1991) Pharm. Res. 8, 1453–1460]. Therefore, the size and the hydrophilic nature of proteins and peptides combine to severely restrict their transport across mucosal barriers.

One approach that has been used to alter the physical nature of the mucosal barriers is the use of penetration enhancers. The use of penetration enhancers is based on the disruption of the cell barriers by the use of low molecular weight agents which can fluidize cell membranes [Kaji, H. et al. (1985) Life Sci. 37, 523–530], open tight junctions [Inagaki, M. et al. (1985) Rhinology 23, 213–221], and create pores in the cell membrane [Gordon, S. et al. (1985) Proc. Natl. Acad. Sci. USA 82, 7419–7423; Lee, V. H. L et al. (1991) Critical Reviews in Therapeutic Drug Carrier Systems, CRC Press 8, 91–192]. The use of these agents leads to a non-specific loss of barrier integrity and can lead to the absorption of a variety of large molecules which can be toxic to cells in vivo.

Protease inhibitors have been co-administered with proteins and peptides and have shown some limited activity in enhancing the absorption of these macromolecules in vivo [Kidron, M. et al. (1982) Life Sci. 31, 2837–2841; Takaroi, K. et al. (1986) Biochem. Biophys. Res. Comm. 137, 682–687]. The safety and the long term effects of this approach have yet to be thoroughly investigated.

The prodrug approach is based on the modifications of peptides in a manner that will protect them from enzyme degradation and recognition. This has been achieved by substitution of the D-forms of amino acids in the structure of peptides, the blockage of vulnerable groups on peptides by amidation and acylation, the inversion of the chirality of peptides, and the introduction of conformational constraints in the peptide structure. The synthesis of prodrugs is only applicable to small peptides which have easily identifiable domains of activity.

Reduction in size is another feasible approach to increasing the transport potential of proteins. However, the active sites of proteins need to be mapped before size reduction can be attempted. In general, this approach is difficult to apply to the majority of proteins.

Carrier ligands, by virtue of their properties, can alter the cell uptake and transport characteristics of proteins and peptides. The essence of this approach is that a cell-impermeant protein or peptide is covalently attached to a carrier which is highly transported into cells. The mechanisms through which carrier ligands become endocytosed and transcytosed are important in deciding the suitability of the carrier for enhancing the transport of proteins and peptides. Macromolecular carriers are hydrophilic and do not partition into the membrane. Therefore, the transport of large polymeric carriers into the cells is mediated by the affinity of the carrier for the cell membrane. Generally, the uptake of a macromolecular conjugate starts with the binding to the cell membrane. The binding of the carrier to the cells can be specific (e.g. binding of antibodies to cell surface antigens), nonspecific (binding of cationic ligands or lectins to cell surface sugars), or receptor mediated (binding of transferrin or insulin to their receptors). Once the carrier is bound to the cell surface, it is taken up into vesicles. These vesicles then become processed stepwise and can be routed to several pathways. One pathway is the recycling of the vesicle back to the membrane from which it was invaginated. Another pathway, which is destructive to the conjugate, is the fusion with lysosomes. An alternative pathway, and one which leads to the transcytosis of the conjugate, is the fusion of the vesicle with the membrane opposite to the side from which it was derived.

The correct balance between the processes of endocytosis and transcytosis determine the delivery of a protein conjugate to its target. For instance, endocytosis may determine the extent to which a conjugate is taken up by the target cell, but transcytosis determines whether or not a conjugate reaches its target [Shen et al. (1992), supra]. For successful absorption through the GI-tract, a conjugate must bind the apical membrane of the. GI-mucosa, become internalized into the mucosal cells, be delivered across the cells, and finally become released from the basolateral membrane.

The current literature contains many reports which demonstrate that nonspecific carriers, such as polylysines [Shen, W. C., and Ryser, H. J. P. (1981) *Proc. Natl. Acad. Sci. USA* 78 7589–7593] and lectins [Broadwell, R. D. et al. (1988) *Proc. Natl. Acad. Sci. USA* 85, 632–646], and specific carriers, such as transferrin [Wan, J. et al. (1992) *J. Biol. Chem.* 267, 13446–13450], asialoglycoprotein [Seth, R. et al. (1993) *J. Infect. Diseases* 168, 994–999], and antibodies [Vitetta, E. S. (1990) *J. Clin. Immunol.* 10, 15S–18S] can enhance the endocytosis of proteins into cells. Reports dealing with transcytotic carriers for proteins are fewer, and very few studies have quantitated the transport of protein conjugates across cell barriers. Wheat germ agglutinin [Broadwell et al. (1988), supra] and an anti-transferrin/methotrexate conjugate [Friden, P. M., and Walus, L. R. (1993) *Adv. Exp. Med. Biol.* 331, 129–136] have been shown to be transcytosed across the blood brain barrier in vivo. Also, polylysine conjugates of horseradish peroxidase (HRP) and a transferrin conjugate of HRP have been shown to be transcytosed across cell monolayers in vitro [Wan, J. and Shen, W. C. (1991) *Pharm. Res.* 8, S-5; Taub, M. E., and Shen, W. C. (1992) *J. Cell. Physiol.* 150, 283–290; Wan, J. et al. (1992) *J. Biol. Chem.* 267, 13446–13450, supra].

Fatty acids, as constituents of phospholipids, make up the bulk of cell membranes. They are available commercially and are relatively cheap. Due to their lipidic nature, fatty acids can easily partition into and interact with the cell membrane in a non-toxic way. Therefore, fatty acids represent potentially the most useful carrier ligands for the delivery of proteins and peptides. Strategies that may use fatty acids in the delivery of proteins and peptides include the covalent modification of proteins and peptides and the use of fatty acid emulsions.

Some studies have reported the successful use of fatty acid emulsions to deliver peptide and proteins in vivo [Yoshikawa, H. et al. (1985) *Pharm. Res.* 2, 249–251; Fix, J. A. et al. *Am. J. Physiol.* 251, G332–G340]. The mechanism through which fatty acid emulsions may promote the absorption of proteins and peptides is not yet known. Fatty acid emulsions may open tight junctions, solubilize membranes, disguise the proteins and peptides from the GI environment, and carry proteins and peptides across the GI-mucosa as part of their absorption [Smith, P. et al. (1992) *Adv. Drug Delivery Rev.* 8, 253–290]. The latter mechanism has been proposed, but is inconsistent with current knowledge about the mechanism of fat absorption.

A more logical strategy to deliver proteins and peptides across the GI-epithelium is to make use of fatty acids as non-specific membrane adsorbing agents. Several studies have shown that a non-specific membrane binding agent linked to a protein can promote the transcytosis of a protein conjugate across cells in vitro [Wan, J. et al. (1990) *J. Cell. Physiol.* 145, 9–15; Taub and Shen (1992), supra]. Fatty acid conjugation has also been demonstrated to improve the uptake of macromolecules into and across cell membranes [Letsinger, R. et al. (1989) *Proc. Natl. Acad. Sci. USA* 86, 6553–6556; Kabanov, A. et al. (1989) *Protein Eng.* 3, 39–42]. Nonetheless, there have been difficulties in conjugating fatty acids to peptides and proteins, including: (1) the lack of solubility of fatty acids in the aqueous solution for the conjugation reaction; (2) the loss of biological activity of peptides and proteins after fatty acid acylation; and (3) the lack of solubilitty of fatty acid-conjugated peptides in aqueous solutions [see, e.g., Hashimoto, M. et al., *Pharm. Res.* 6, 171–176 (1989); Martins, M. B. F. et al., *Biochimie* 72, 671–675 (1990); Muranishi, S. et al., *Pharm. Res.* 8, 649–652 (1991); Robert, S. et al., *Biochem. Biophys. Res. Commun.* 196, 447–454 (1993)].

It is an object of the present invention to provide methods and compositions for use in conjugating fatty acids to hydrophilic molecules and in improving the bioavailability of peptides and proteins.

SUMMARY OF THE INVENTION

In accordance with the present invention, fatty acid derivatives of sulfhydryl-containing compounds (for example, peptides, proteins or oligonucleotides which contain or are modified to contain sulfhydryl groups) comprising fatty acid-conjugated products with a disulfide linkage are employed for delivery of the sulfhydryl-containing compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties. Reagents and methods for preparation of the fatty acid derivatives are also provided.

BRIEF DESCRIPTION OF THE DRAWINGS

The invention may be better understood with reference to the accompanying drawings, in which.

DETAILED DESCRIPTION OF THE INVENTION

Figure 1:
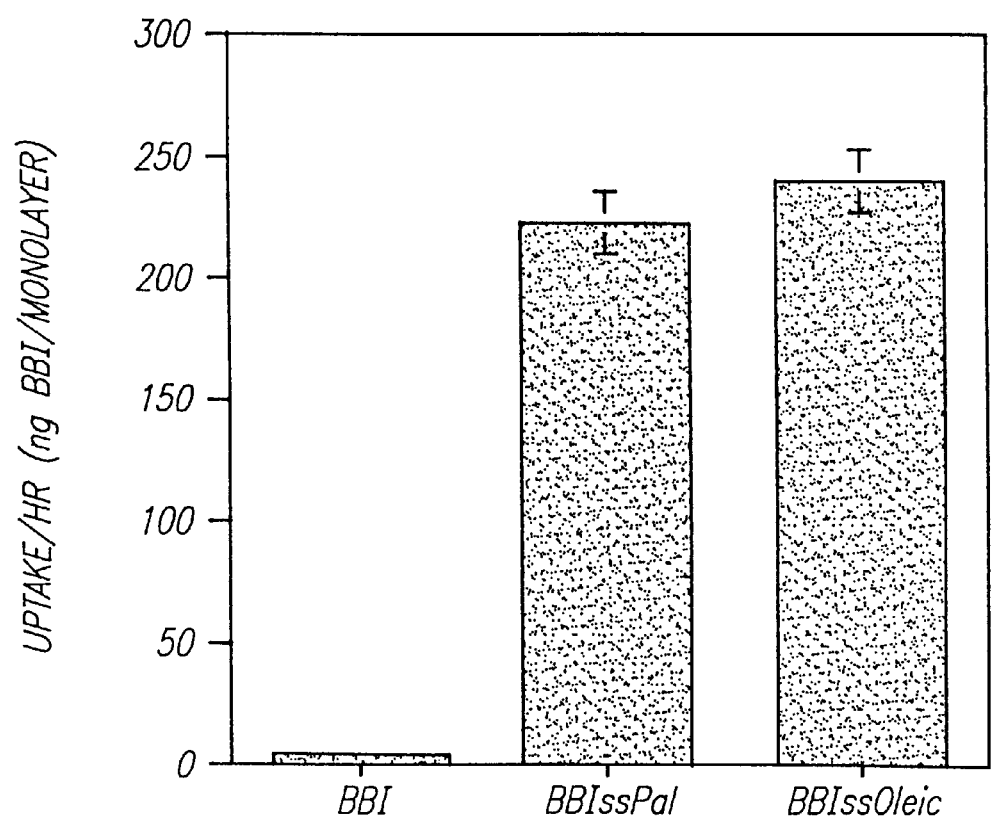
FIG. 1 illustrates the uptake of BBI, BBIssPal and BBIssOleic in Caco-2 cells.
Figure 2A:
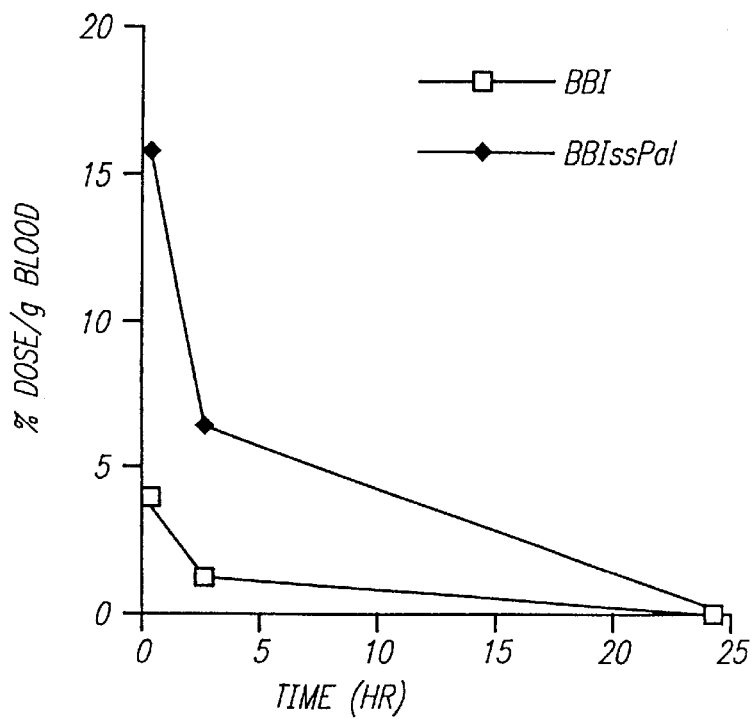
FIG. 2 illustrates biodistribution of BBI and BBIssPal in blood, kidneys, lungs and liver of CF-1 mice following iv-administration.
Figure 2B:
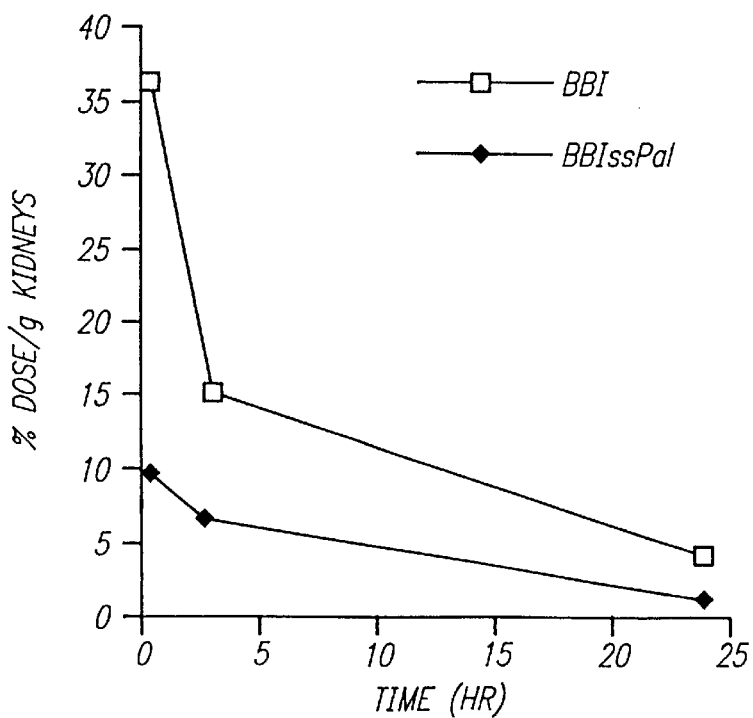
Figure 2C:
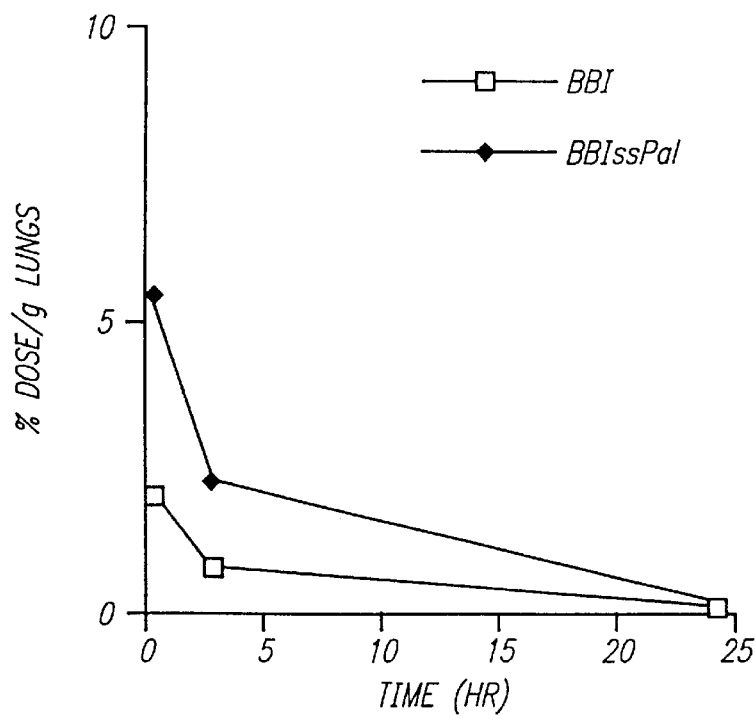
Figure 2D:
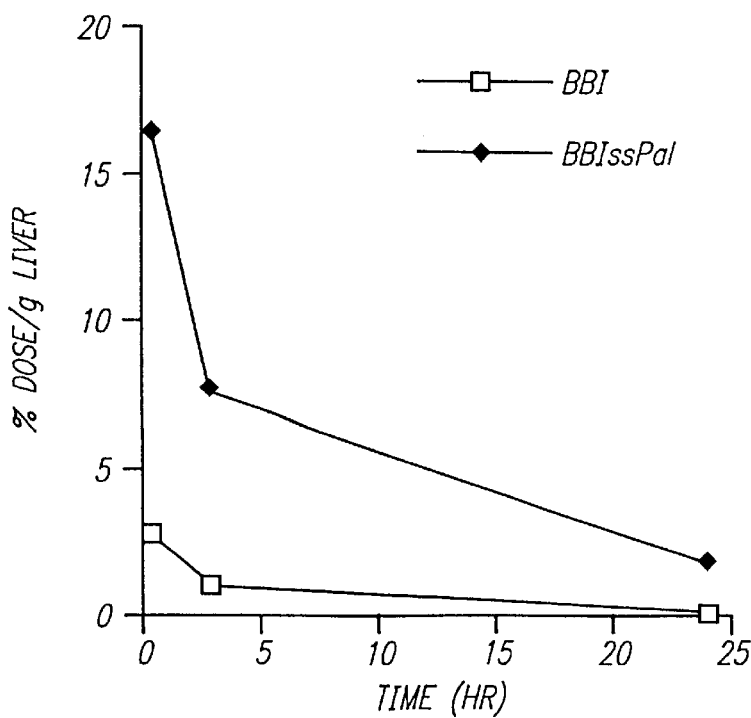
Figure 3A:
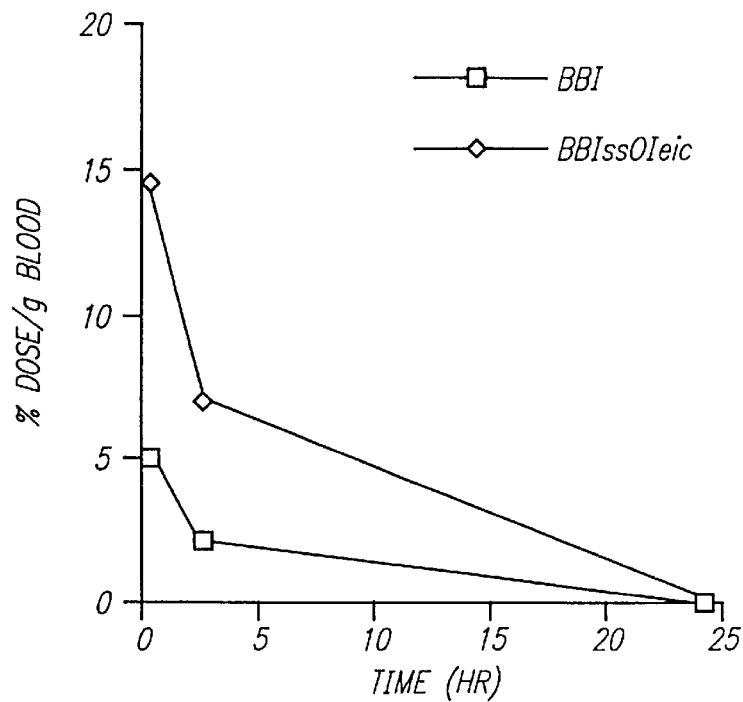
FIG. 3 illustrates biodistribution of BBI and BBIssOleic in blood, kidneys, lungs and liver of CF-1 mice following iv-administration.
Figure 3B:
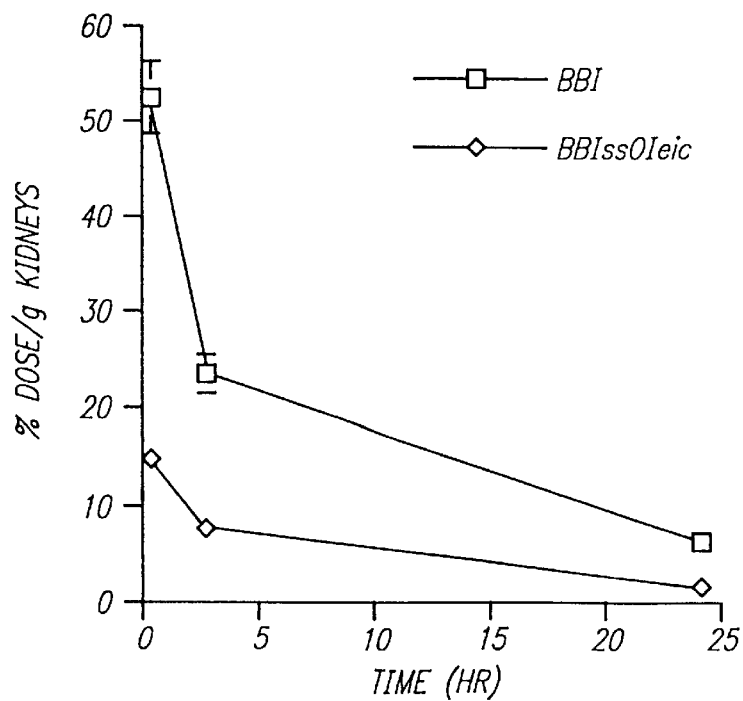
Figure 3C:
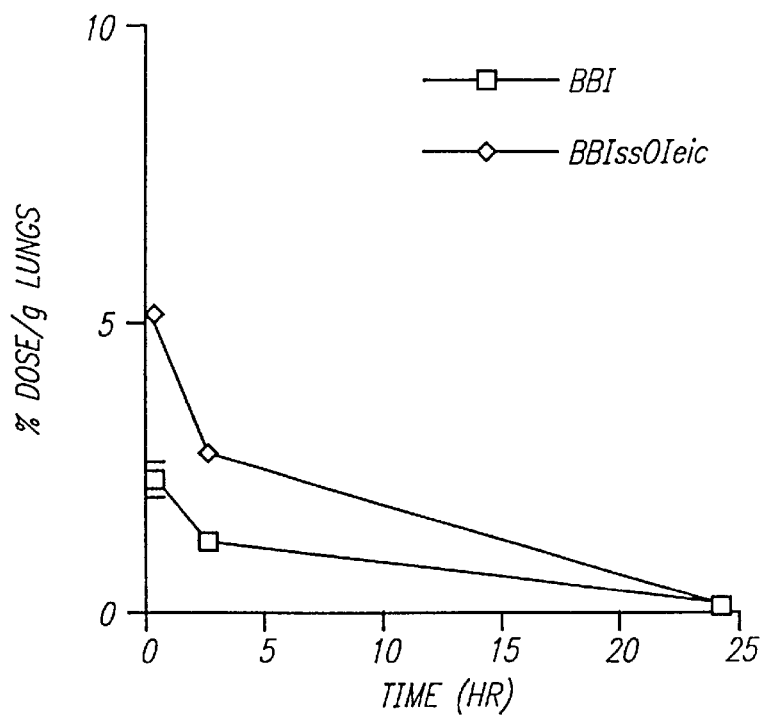
Figure 3D:
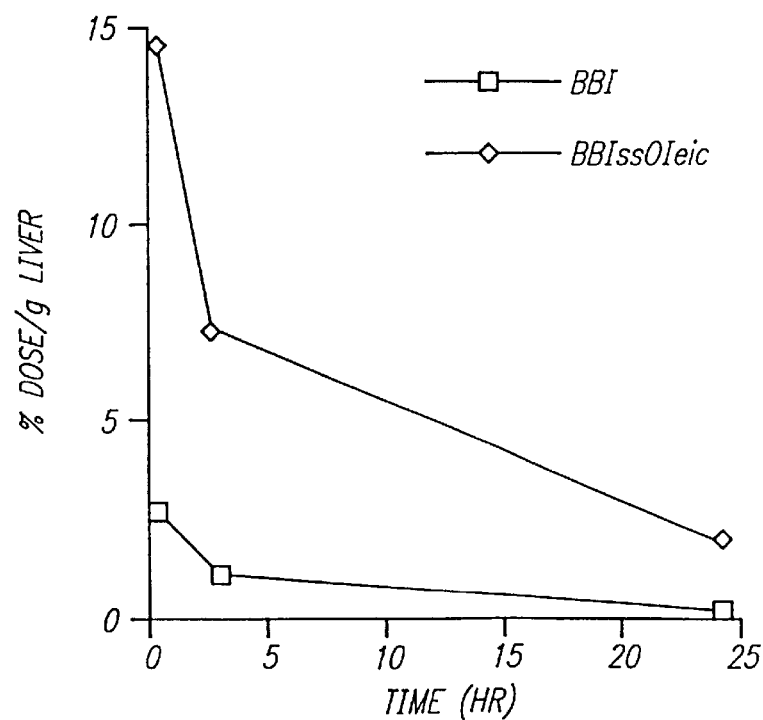

Pursuant to the present invention, a sulfhydryl-containing compound (for example, a biopolymer as hereinafter defined) is attached to a fatty acid derivative via a reversible, biodegradable disulfide bond. Such a conjugate would be expected to bind to the apical side of a cell membrane, reach the basolateral membrane of the GI-epithelium as a result of membrane transport and turnover, and become released into interstitial fluid as the result of disulfide bond reduction.

Pursuant to one aspect of the present invention, there are provided conjugates of the general formula VI

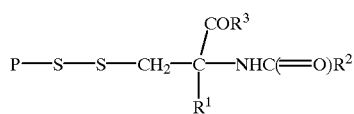
VI in which P is a residue derived from a sulfhydryl-containing compound; $R^1$ is hydrogen, lower alkyl or aryl; $R^1$ is a lipid-containing moiety (as hereinafter defined); and $R^3$ is —OH, a lipid-containing moiety or an amino acid chain comprising one or 2 amino acids and terminating in —CO$_2$H or —COR$^2$. These conjugates are particularly useful for increasing the absorption and prolonging blood and tissue retention of the sulfhydryl-containing compound PSH.

Pursuant to another aspect of the present invention, methods for increasing the absorption or prolonging blood and tissue retention in a mammal of a sulfhydryl-containing compound of the general formula PSH are provided, in which a conjugate of general formula VI is formed from the sulfhydryl-containing compound and the conjugate is then administered to the mammal (for example, in an aqueous solution or an oral dosage unit).

Pursuant to yet another aspect of the present invention, there are provided compounds of the general formula V

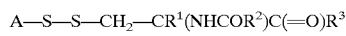
V in which A is an aromatic activating residue (as hereinafter defined) and $R^1$, $R^2$ and $R^3$ are as previously defined. The compounds of general formula V are particularly useful in preparation of conjugates of general formula VI from sulfhydryl-containing compounds of general formula PSH.

Pursuant to still another aspect of the present invention, there are provided method for forming conjugates of general formula VI from sulfhydryl-containing compounds of general formula PSH, which comprises reacting a compound of general formula PSH with a compound of general formula V. The reaction is typically carried out with an excess (e.g., a two-fold to a ten-fold excess) of the compound of general formula V for a period of time of about 1 hour to about 24 hours at a temperature of about 4° C. to about 37° C. in a suitable aqueous buffer solution (e.g., phosphate, bicarbonate and borate buffers). Preferably, the reaction is carried out in bicarbonate buffer, pH 8.

Pursuant to another aspect of the present invention, there are provided compounds of the general formula III

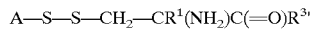
III in which $R^{3'}$ is —OH or an amino acid chain comprising one or two amino acids and terminating in —CO$_2$H and A and $R^1$ are as previously defined. The compounds of general formula III are useful in preparing the compounds of general formula V. The compounds of general formula III are suitably prepared by reacting a compound of general formula II

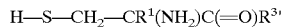
II with a compound of general formula A—S—S—A or A—S—S—A', in which A' is different from A and is an aromatic activating residue. These reactants are either commercially available [e.g., 2,2'-dithiopyridine and 5,5'-dithiobis(2-nitrobenzoic acid)]or may be prepared by routine synthetic procedures well known to those skilled in the art.

Pursuant to still another aspect of the present invention, there are provided methods for preparation of compounds of general formula V in which $R^2$ is a lipid group, wherein a compound of general formula III is reacted with an activated lipid group of general formula X—O$_2$C—B or X—OC—B, in which X is a lipid-activating group (as hereinafter defined) and B is a lipid group (as hereinafter defined). Compounds of general formula X—O$_2$C—B or X—OC—B may be readily prepared in a manner known per se.

For preparation of a compound of general formula III, in an exemplary procedure generally equal molar quantities of a compound of general formula II and a compound of formula A—S—S—A or A—S—S—A' may suitably be mixed in a polar organic solvent (e.g., ethanol). The product of general formula III may then suitably be isolated by crystallization from a nonpolar organic solvent (e.g., benzene). Of course, other suitable procedures would also be evident to those working in the field.

For preparation of X—O$_2$C—B or X—OC—B, a fatty acid may for example be reacted with: (a) N-hydroxysuccinimide and a carbodiimide reagent to form an H-hydroxysuccinimidyl active ester; (b) trifluoroacetic anhydride to form a fatty acid anhydride; or (c) thionyl chloride to form a fatty acid chloride. Alternative procedures may also suitably be employed to introduce these or other lipid-activating groups.

For purposes of the present invention, the term "lipid-containing moiety" refers to either a lipid group per se or a hydrocarbon-based group (in particular, one or more amino acids) comprising a lipid group. By the term "lipid group" is meant a hydrophobic substituent consisting of 4 to 26 carbon atoms, preferably 5 to 19 carbon atoms. Suitable lipid groups include, but are not limited to, the following: palmityl ($C_{15}H_{31}$); oleyl ($C_{15}H_{29}$); stearyl ($C_{17}H_{35}$); cholate; and deoxycholate.

By "aromatic activating residue" is meant a moiety which serves to make the disulfide group of the compounds of general formula V more labile to the displacement reaction with the sulfhydryl-containing compounds of general formula PSH (and thus, serves as a good leaving group). A presently preferred aromatic activating group is 2-pyridyl; other suitable aromatic activating groups include 4-nitrophenyl.

The term "lipid-activating group" refers for purposes of the present invention to a moiety which renders a carboxy-lipid group to which it is attached reactive with a compound of general formula III. A presently preferred lipid-activating group is N-hydroxysuccinimidyl ester; other suitable lipid-activating groups include acid chloride and acid anhydride.

While the present invention contemplates the preparation and use of conjugates of general formula VI comprising a wide range of compounds containing sulfhydryl groups, it is particularly advantageous to employ the methods and compositions of the present invention for preparation of conjugates comprising biopolymers. Biopolymers of interest include peptides, proteins, and oligonucleotides (as hereinafter defined). As would be readily apparent to those working in the field biopolymers or thiolated biopolymers containing sulfhydryl groups may comprise a plurality of moieties corresponding in structure to the conjugates of general formula VI (i.e., groups having the structure of the compounds of general formula VI minus the moiety P).

For purposes of the present invention, the term "peptide" refers to amino acid chains comprising two to 50 amino acids and the term "protein" to amino acid chains comprising more than 50 amino acids. The proteins and peptides may be isolated from natural sources or prepared by means well known in the art, such as recombinant DNA technology or solid-state synthesis. It is contemplated that the peptides and proteins used in accordance with the present invention may comprise only naturally-occurring L-amino acids, combinations of L-amino acids and other amino acids (including R-amino acids and modified amino acids), or only amino acids other than L-amino acids. In order to form a conjugate of general formula I, the peptide or protein must bear at least one reactive thiol group. In many cases, the peptide or protein contains cysteine residues (an amino acid comprising a thiol group). A peptide or protein which does not contain a thiol group may be modified by procedures well known per se to those working in the field, in particular, well known thiolating agents [e.g., N-succinimidyl-3-(2-pyridyldithio)propionate (SPDP) and 2-iminothiolane (Traut's reagent)] may be routinely employed for this purpose.

The term "oligonucleotide" refers to chains comprising two or more naturally-occurring or modified nucleic acids, for example naturally-occurring or recombinant deoxyribonucleic acids (DNA) and ribonucleic acid (RNA) sequences. For formation of a conjugate in accordance with the present invention, the oligonucleotide must be modified by thiolating reactions so as to contain a sulfhydryl group for linking with the lipid-containing moiety. Such modifications may be routinely carried out in a manner known per se. For example, an oligonucleotide may be coupled to cystamine using carbodiimide and subsequently reduced by dithiothreitol to generate a free sulfhydryl group.

In one preferred class of compounds of general formula VI, $R^1$ is hydrogen. $R^2$ is a lipid moiety and $R^3$ is —OH. This type of conjugate is suitably derived from cysteine. In another preferred class of conjugate in accordance with the present invention, $R^1$ is hydrogen, $R^2$ is —$CH_2CH_2CH(NH_2)CO_2H$ or —$CH_2CH_2CH(NHCO$-lipid$)CO$-lipid and $R^3$ is —$NHCH_2CO_2H$ or —$NHCH_2CO$-lipid in which at least one of $R^2$ and $R^3$ comprises a lipid moiety. This type of conjugate is suitably derived from glutathione.

The synthesis of an exemplary compound of general formula VI (in which P is a protein) is illustrated in Scheme I. Of course, as would be readily appreciated by those skilled in the art, a variety of alternative synthetic schemes could also readily be developed.

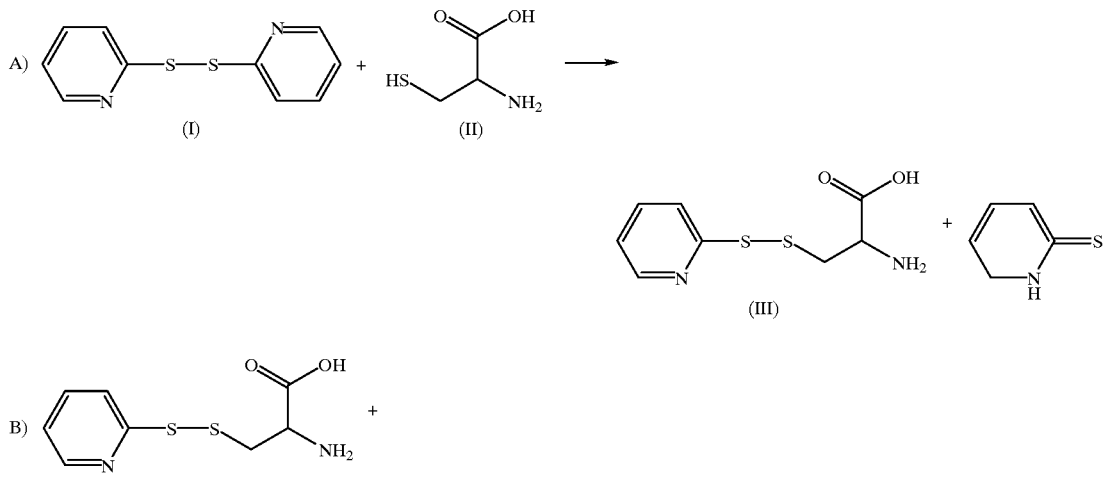

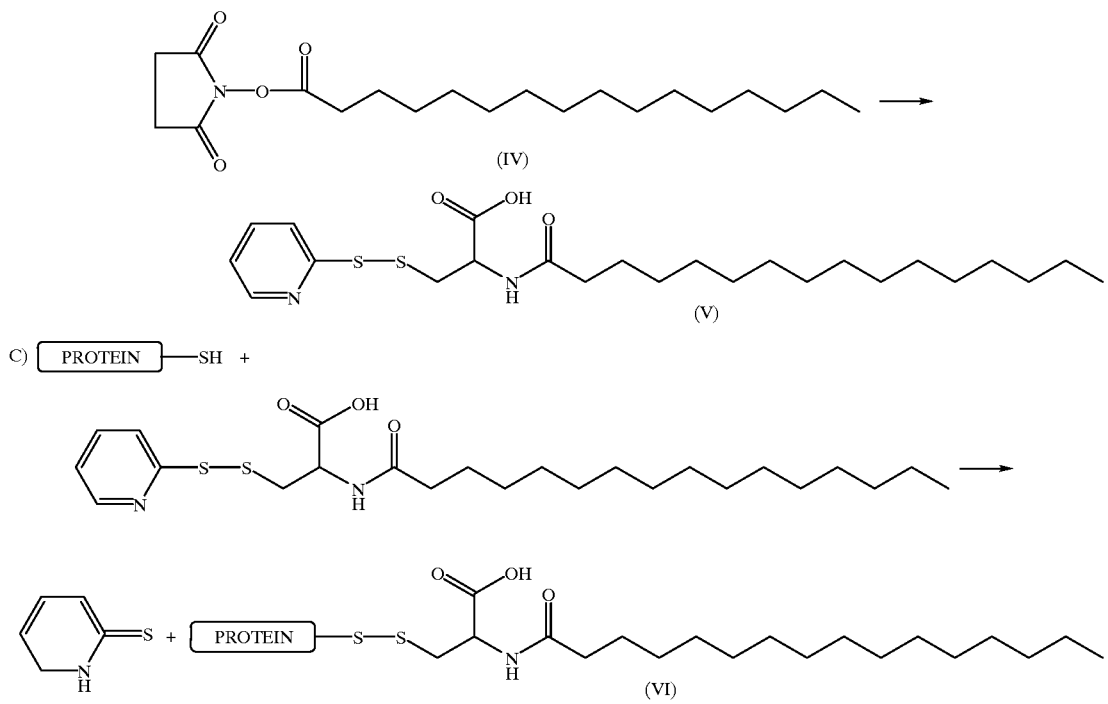

The fatty acid conjugates of the present invention are soluble in most buffer solutions in which proteins and peptides are soluble. In particular, any free carboxylic acid groups are charged at neutral pH and therefore improve the solubility of the conjugates. This greatly facilitates the formulation of the conjugates with suitable pharmaceutically-acceptable carriers or adjuvants for administration of the proteins or peptides to a patient by oral or other routes.

It is a particular advantage in accordance with the present invention that the disulfide linkage between the fatty acid moiety and the peptide or protein may readily be reduced. Therefore, the active peptide or protein molecules are released in intact form inside the target tissues or cells. Furthermore, the fatty acid moiety of the conjugates comprises only amino acids and lipid molecules which are not toxic to mammals, in particular humans.

The invention may be better understood with reference to the accompanying examples, which are intended for purposes of illustration only and should not be construed as in any sense limiting the scope of the invention as defined in the claims appended hereto.

EXAMPLES

Example 1

Synthesis of N-palmityl-2-pyridyldithiocysteine (Pal-PDC)

An ice-cold solution of L-cysteine (I) (3.0 g) in ethanol (50 ml) was added dropwise to a stirred solution of 2,2-dithiopyridine (II) (7.5 g) in ethanol (30 ml), and the reaction was allowed to proceed at 25° C. for 18 hr. The solution was centrifuged in order to remove any precipitate, and the supernatant was reduced in volume to 40 ml using a rotary evaporator. Subsequently, the reaction mixture was added dropwise to 400 ml of ice-cold benzene. PDC (III), which crystallized in benzene, was isolated by filtration, redissolved in 40 ml of ethanol, and then recrystallized in 400 ml of ice-cold benzene as described above. The recrystallized product was isolated by filtration, dried under vacuum overnight, and finally stored at −20° C. in a desiccator.

PDC (100 mg) (III) was dissolved in 5 ml of DMF and mixed with 100 μl of triethylamine, and the resultant suspension was reacted with the N-hydroxysuccinimide ester of palmitic acid (IV) (250 mg) in DMF (5 ml) at 25° C. for 24 hr, during which time the suspension turned clear. This solution was diluted with 40 ml of ice-cold water, pH 3.0, and the precipitate, which contained Pal-PDC (V) and palmitic acid, was isolated by centrifugation at 10000 rpm for 30 min. Pal-PDC (V) was separated from palmitic acid by suspension of the precipitate in water, pH 7.0, which dissolved Pal-PDC (V), but not palmitic acid. Pal-PDC (V) was purified further using two more steps of acid precipitation as described above.

Example 2

Synthesis of Conjugates

Unless otherwise stated, all the final reagents used in the conjugation steps (Pal-PDC and PDC) were analyzed using silica-coated thin layer chromatography (TLC) plates containing fluorescent indicators. These plates were not activated by heating prior to any of the analyses. For the routine analysis of the reagents synthesized, 5 μl of a ethanolic solution containing the reagent (5 mg/ml) was applied to the plates. Subsequently, the plates were developed in solvent chambers, equilibrated with the mobile phase. Once the solvent front had travelled a sufficient distance, the plates were removed, dried, and studied under a UV-lamp. Positions of the spots were marked on the plates immediately, and a drawing of the plate and the spots was made. The Rf value for each spot visualized was calculated and recorded. The composition of the mobile phases used in the analyses were adjusted to provide optimum separation of the reagent-spots.

For purposes of illustration, conjugates of BBI were synthesized. BBI is a hydrophilic protein which has low uptake into cells and is not orally bioavailable. In addition, BBI is stable in the GI tract and resists degradation by the mammalian proteases in the gut [Yavelow, J. et al. (1983) *Cancer. Res.* 43, 2454s–2459s]. The use of BBI for chemoprevention can be accepted only if an orally absorbable form of BBI can be developed.

BBI (20 mg) was dissolved in 1 ml of a sodium bicarbonate solution (0.3 M, pH 8.0) and reacted with SPDP (5 mg/100 μl of DMF) for 2 hr at 25° C. After purification of BBI-PDP using Sephadex® G50 gel-filtration chromatography, the PDP-derivatization of BBI was estimated by measuring the release of the thiopyridine moiety after reduction of BBI-PDP with dithiothreitol (DTT). Using this procedure, approximately 4 amino groups per BBI molecule were modified with SPDP. The level of derivatization of BBI could be controlled by adjusting the pH of the reaction buffer; the modification of BBI could be adjusted from one amine group per BBI molecule when the reaction was carried out at pH 7, to 4.5 amine groups modified when the reaction was carried out at pH 8.5.

BBI-PDP (20 mg) in PBS (1 ml, pH 5.0) was reduced with DTT (25 mM) for 30 min and subsequently eluted from a Sephadex® G50 column. The sulfhydryl-containing BBI fractions, which eluted at the column void volume, were identified using Elman's reagent, and then reacted with a 3-fold excess (per sulfhydryl group on BBI) of Pal-PDC (V) in PBS, pH 7.0, for 16 hrs at 4° C. The reaction mixture was then acidified to pH 3.0 using HCI (1M) and left on ice for 30 min. The supernatant was analyzed separately using a Sephadex G25 gel-filtration column. The precipitate, which contained the palmityl disulfide conjugate of BBI, BBIssPal (VI), and the excess reagent, was isolated by centrifugation, dissolved in DMF (2 ml), and eluted from a Sephadex® LH20 column using DMF. BBIssPal (VI) fractions, which eluted at column void volume, were isolated, dialyzed 3 times against 500 volumes of water, and then lyophilized. The yield of the conjugate using this procedure was approximately 80% (by weight). The conjugation of Pal-PDC to BBI was confirmed and quantitated after the conjugation of [3H]-labeled Pal-PDC (V) to BBI using identical conjugation conditions as the ones described above. Also, using an identical procedure, the oleic acid conjugated BBI (BBIssOleic) was synthesized.

Example 3

Transport of Conjugates

Human colon carcinoma cells (Caco-2) were detached from 25 cm² stock culture flasks using a 10 min incubation at 37° C. with 0.5 ml of a trypsin/EDTA solution (0.5% trypsin, 5.3 mM EDTA). The cells were then suspended in 5 ml of Dulbecco's minimum essential medium, supplemented with 15% fetal bovine serum (FBS), L-glutamine (1%), and essential amino acids (1%), and counted using a coulter counter.

Suspended Caco-2 cells in 1.5 ml of medium were seeded into the apical chamber of the transwells at a density of 0.5 million cells per insert. 2.5 ml of the medium was then added to the basal chambers of each transwell. The cells were allowed to attach for 2 days without disturbance and were then fed every other day until the experiments were performed. The cells were maintained for approximately 14–20 days prior to the experiments and were fed 24 hr before each experiment. The cell monolayers developed a transepithelial electrical resistance (TEER) of approximately 500–600 Ω cm² within one week of the seeding and maintained this resistance for up to 21 days post-seeding.

Radioiodination of BBI and BBIssPal was carried out using the chloramine-T method [McConahey, P. C., and Dixon, F. J. (1980) *Meth. Enzymol.* 70, 221–247]. Confluent, 14-day old cell monolayers were washed once with, and then incubated in, serum-free Dulbecco medium at 37° C. for 30 min. Subsequently, the incubation medium was replaced with serum free medium containing $^{125}$I-BBI (10 μg/ml), either as native-BBI or as BBIssPal or BBIssOleic, and the monolayers were incubated for a further 60 min at 37° C. The monolayers were then washed three times with ice-cold PBS, and then exposed to trypsin (0.5%, EDTA 5.3 mM) for 10 min at 37° C. The detached cells were transferred to tubes, isolated by centrifugation, washed three times using ice-cold PBS, assayed for accumulated radioactivity using a gamma counter, and finally assayed for cell protein using the published method [Lowry, O. H. et al. (1951) *J. Biol. Chem.* 193, 265–275].

In some experiments the uptake of reduced $^{125}$I-BBIssPal into cells was determined. $^{125}$I-BBIssPal was reduced with DTT (50 mM) at 60° C. for 5 min followed by a further 25 min at 37° C. In control experiments, $^{125}$I-BBIssPal was exposed in medium to the same temperatures without being exposed to DTT.

The uptake of $^{125}$I-BBIssPal in the presence of BSA (fatty acid free) was determined as follows. $^{125}$I-BBIssPal was incubated with medium containing 0.1% BSA for 30 min at 37° C. before being added to the cell monolayers. In some uptake experiments, BSA was first mixed with a 3 fold molar excess of palmitic acid, and then incubated with the conjugates prior to the experiments. In the experiments where the uptake of $^{125}$I-BBIssPal was determined in medium containing FBS, the conjugates was simply added to the medium containing the required amount of FBS.

Confluent cell monolayers, 2 to 3 weeks old, and having a TEER value of approximately 500 Ω cm², were first incubated with Dulbecco's MEM containing 1% of FBS for 30 min at 37° C. Subsequently, the incubation medium was removed, and the $^{125}$I-BBI (10 μg/ml) conjugates in 1.5 ml of the medium was added to the apical chamber of the transwells. To the basal chamber. 2.5 ml of the medium was added and the transwells were incubated at 37° C. At predetermined times, the entire basal chamber medium (2.5 ml) from each transwell was removed and counted for radioactivity using a gamma counter. In each experiment, typically seven samples were taken at 1, 2, 3, 4, 5, 6 and 24 hr post-incubation. After the 24 hr samples were taken, the cell monolayers were rinsed three times with ice-cold PBS, cut out of the inserts, and counted for accumulated radioactivity using a gamma counter.

The integrity of the $^{125}$I-BBI conjugates transported across the monolayers was studied using Sephadex G50 gel-filtration chromatography. Briefly, after the basal medium was sampled at 24 hr, 1.0 ml of the medium was centrifuged at 2000 rpm and then eluted from a G50 column (10 ml) using PBS; 1 ml fractions were collected and the fraction-associated radioactivity was determined using a gamma counter. Intact conjugates eluted at column void volume and fragments smaller than 1 kDa were eluted at or above the column volume.

The results of the uptake of $^{125}$I-BBI, either as the free protein or in conjugated form to palmitic acid, in the presence of different amounts of added FBS are shown in Table 1. When the conjugates were incubated with the cells in serum-free medium, the uptake of BBIssPal was approximately 140-fold higher than that of BBI. In the presence of medium containing 1% FBS, the internalization of BBIssPal was increased by 35-fold over that of BBI. Increasing the serum concentration further to 10%, caused a further decrease in the uptake of BBIssPal into the cells to only a 10-fold higher level than that of native-BBI. The internalization of BBIssPal into Caco-2 cells was reduced drastically in the presence of serum to 14% and 2.3% of that of the serum-free values for 1% and 10% FBS containing media, respectively.

TABLE 1

| | Uptake (ng BBI/mg of cell protein)/hr | | |
|---|---|---|---|
| | serum free | 1% FBS | 10% FBS |
| BBI | 3.9 ± 0.19 | 2.2 ± 0.17 | 1.3 ± 0.02 |
| BBIssPal | 540.0 ± 24.13 | 78.5 ± 3.41 | 12.9 ± 0.02 |

The cell monolayers were incubated with $^{125}$I-labeled conjugates at 10 μg/ml for 60 min at 37° C. The results presented are the average of three monolayers ±SEM. The uptake experiments were carried out in Dulbecco medium, in the presence and absence of added FBS.

Since the BBIssPal uptake into the cells was believed to be mediated by the palmitic acid ligands on the conjugate, the uptake of $^{125}$I-BBIssPal into Caco-2 cells before and after reduction with DTT was studied. Since the presence of serum in the incubation medium had an inhibiting effect on the uptake of the conjugates into the cells, the uptake was studied in serum-free medium. The results are shown in Table 2. The uptake of untreated $^{125}$I-BBIssPal into the cells was 80-fold higher than that of $^{125}$I-BBI. The exposure of $^{125}$I-BBI to DTT did not cause a reduction in the uptake. In contrast, the reduction of $^{125}$I-BBIssPal with DTT reduced the uptake of the conjugate in to the cells by approximately 80%. The reduction of BBIssPal with DTT causes the detachment of the palmitic acid from the conjugate. Hence, the uptake of $^{125}$I-BBIssPal was mediated by the hydrophobic palmitic acid ligand.

TABLE 2

| | Uptake (ng BBI/mg of cell protein)/hr | |
|---|---|---|
| | Untreated | DTI-treated |
| BBI | 4.8 ± 0.00 | 5.2 ± 0.00 |
| BBIssPal | 381.7 ± 0.03 | 46.5 ± 0.00 |

The cell uptake of $^{125}$I-BBI, either as the native protein or as BBIssPal was determined before and after reduction with DOT (50 mM) for S min at 60° C. and 25 min at 37° C.

Bovine serum albumin (BSA) is known to be a carrier of fatty acids in vivo and contain hydrophobic regions which can tightly bind fatty acids. Since the uptake of $^{125}$I-BBIssPal was reduced in the presence of serum, the possibility that BBIssPal bound to BSA present in FBS was investigated. The cell uptake of $^{125}$I-BBIssPal and $^{125}$I-BBI in the presence of medium containing fat-free BSA or fatty acid-loaded BSA was studied, and the results are shown in Table 3. In the presence of BSA-free medium, the uptake of $^{125}$I-BBIssPal into the cells was 80-fold higher than that of BBI, as was expected from the results obtained in the previous experiments. When defatted-BSA (fatty acid-free BSA) (0.1%) was present in the medium, the uptake of $^{125}$I-BBIssPal was reduced by 82%, whereas the uptake of $^{125}$I-BBI was not affected. In the presence of fatty acid-loaded BSA (0.1%), which was produced by spiking fat-free BSA with a 3-molar excess of palmitic acid, the uptake of $^{125}$I-BBI was again not affected. Therefore, $^{125}$I-BBIssPal binds strongly to BSA and this binding is dependent on the number of fatty acids already bound to BSA.

TABLE 3

| | Uptake (ng BBI/mg of cell protein)/hr | | |
|---|---|---|---|
| | serum free | BSA | BSA/FA |
| BBI | 4.8 ± 0.00 | 4.8 ± 0.00 | 3.9 ± 0.00 |
| BBIssPal | 380.0 ± 0.03 | 69.7 ± 0.00 | 258.9 ± 0.00 |

The uptake experiments were carried out in Dulbecco medium, in the presence and absence of added fatty acid-free BSA (BSA) or fatty acid-loaded BSA (BSA/FA). The results of studies of the uptake of $^{125}$I-BBI, either as the native-BBI or in conjugated form to palmitic or oleic acid, in Caco-2 cells in the presence of serum-free medium are presented in FIG. 1. The results are shown as the average ng of BBI internalized ±SEM, n=3. The uptake of $^{125}$I-BBIssPal into the cells was approximately 100-fold higher than that of $^{125}$I-BBI. Similarly, the uptake of $^{125}$I-BBIssOleic into the cells was about 108-fold higher than $^{125}$BBI. The difference between the uptake of $^{125}$I-BBIssPal and $^{125}$I-BBIssOleic were not significant.

Example 4

Biodistribution Assays

Female CF-1 mice, 2 to 3 weeks old, weighing 20–25 g each, with free access to food and water prior to the experiments, were used for the animal experiments. $^{125}$I-BBI (3 mg/kg), as native-BBI or as BBIssPal or BBIssOleic conjugate, was administered to the animals via the tail vein. At 0.5, 3, and 24 hr post-injection, 3 animals from each experiment group were sacrificed and their blood (200 μl), the kidneys, the lungs, and the liver were removed, rinsed in ice-cold PBS, and assayed for accumulated radioactivity. The weights of the organs were recorded and used to adjust the concentration of the conjugates in the organs.

In the ip-biodistribution studies, $^{125}$I-BBI (3 mg/kg), either as the native-BBI or as BBIssPal, was administered into the lower left quadrant of the abdominal cavity of each animal. The animals were then treated in the manner described for the iv.-biodistribution studies.

The results of the biodistribution of BBI and BBIssPal following iv-administration are shown in FIG. 2 as the % dose accumulated per g organ ±SEM. The results indicated that while BBI was rapidly excreted from the body without attaining high blood levels, BBIssPal was accumulated in the blood at a relatively high level and was apparently more slowly removed form the circulation. The kidney biodistribution results indicated that while BBI was rapidly accumulated in the kidneys, BBIssPal was not. The liver accumulation of BBIssPal was approximately 5-fold higher than that of BBI, and BBIssPal levels remained high in the liver even at 24 hr post-injection. The lung accumulation of BBIssPal was also approximately 2-fold higher than that of BBI, but this result may have been caused by the residual blood present in the organ after its excision. Clearly, BBIssPal was retained longer and at a higher level in the blood and the liver. On the other hand, the kidney clearance of BBIssPal was about 4-fold lower than native-BBI.

The iv-biodistribution of BBI and BBIssOleic were also studied in CF-1 mice. The results are presented in FIG. 3 as the % dose accumulated per g of the organ ±SEM, n=3, at 0.5, 3 and 24 hr. The biodistribution of BBIssOleic was very similar to BBIssPal. As was observed for BBIssPal, BBIssOleic had higher blood levels than BBI and was apparently more slowly cleared from the circulation. The blood levels of BBIssOleic were about 4-fold higher than those of BBI at the same time points. The kidney clearance of BBIssOleic was approximately 4-fold lower, and the liver accumulation approximately 4-fold higher than native-BBI. The retention of BBIssOleic in the liver was prolonged, with significant levels of the conjugate present in the liver even at 24 hr post-injection. The lung levels of BBIssOleic were about 2-fold higher than native-BBI levels, but the higher residual blood in the lungs could account for this observation.

Figure 4A:
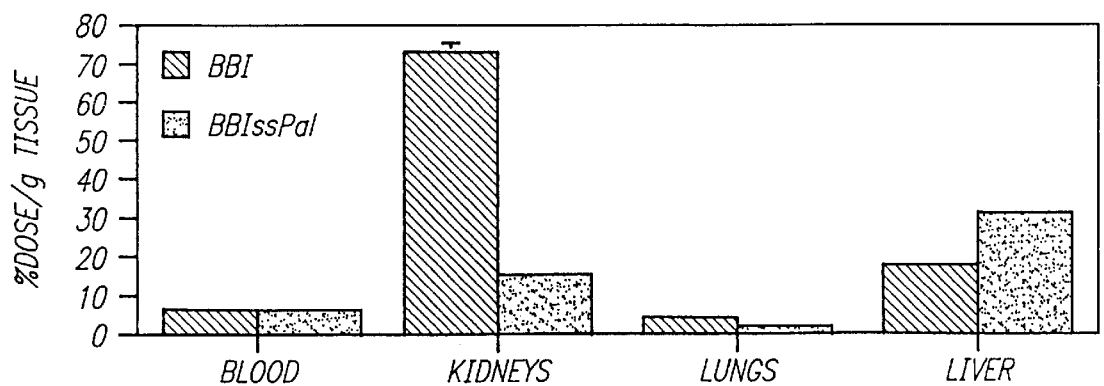
FIG. 4 illustrates biodistribution of BBI and BBIssPal in CF-1 mice following ip-administration.
Figure 4B:
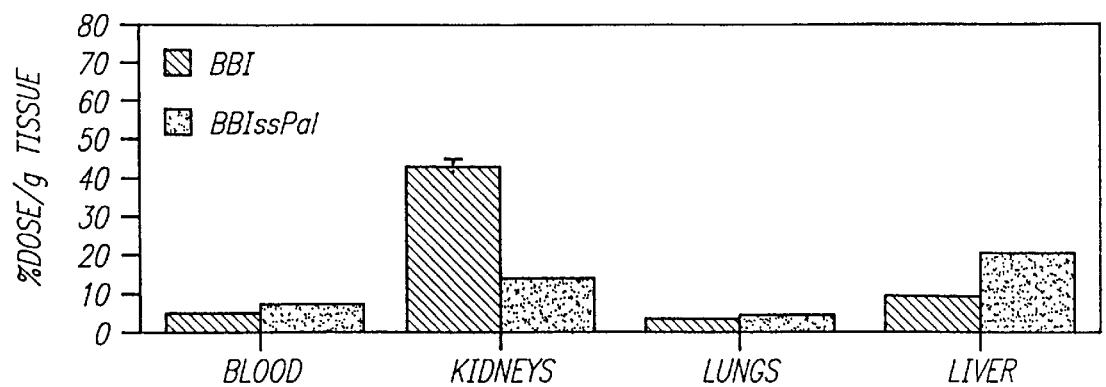
Figure 4C:
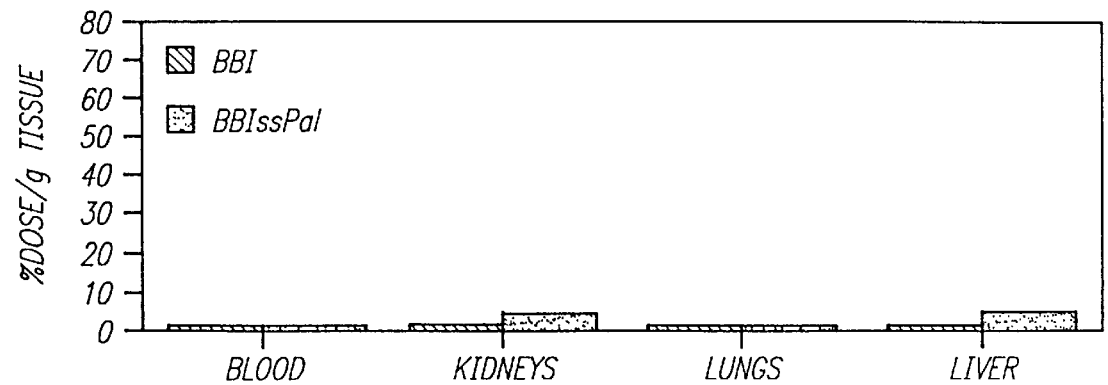

The ip-biodistribution of $^{125}$I-BBIssPal in CF-1 mice is shown in FIG. 4 as the average % dose accumulation per organ ±range (bars) at 0.5 hr (FIG. 4A), 3 hr (FIG. 4B) or 24 hr post-injection (FIG. 4C). The kidney accumulation of $^{125}$I-BBIssPal was 4-fold lower than that of native $^{125}$I-BBI for the 0.5 and 3 hr time points. At 24 hr, $^{125}$I-BBIssPal levels were higher in the kidneys than $^{125}$I-BBI. The blood level of $^{125}$I-BBIssPal was similar to that of $^{125}$I-BBI at 0.5 hr, 1.5-fold higher than BBI at 3 hr, and approximately 3-fold higher than BBI at 24 hr. The liver accumulation of $^{125}$I-BBIssPal was 1.5-fold higher than $^{125}$I-BBI at 0.5 hr, 2.5-fold higher at 3 hr, and about 4-fold higher at 24 hr. Relatively large amounts of $^{125}$I-BBIssPal were present in the liver and the kidneys at 24 hr.

Example 5

In Vitro Transformation Studies

Transformation assays were carried out using C3H 10T1/2(clone 8) cells according to the published recommendations [Reznikoff, C. A et al. (1973) Cancer. Res. 33, 3239–3249; Reznikoff, C. A. et al. (1973) Cancer. Res. 33, 3231–3238]. Stock cultures of mycoplasma-free cells were maintained by passing 50,000 cells per 75 cm$^2$ flask every seven days. Using this schedule, the cells were always passed approximately 2 days before reaching confluence. The stock culture was grown in Eagle's basal medium supplemented with 10% FBS, penicillin (100 units), and streptomycin (100 μg) and used for the transformation assays at passages of 9 to 14. The cells were passed by treating the stock cells with trypsin (0.1%) in PBS for 5 min and quenching the trypsin with 5 ml of the medium. This procedure was adapted to minimize spontaneous transformation in the stock cultures and maximize the plating efficiency in the petri dishes. The FBS stock used in the cultures was pre-screened to ensure that the serum was able to support the expression and the growth of the transformed cells.

For the transformation assays, C3H 10T1/2 cells (1000/dish) were seeded into 60 mm petri dishes and allowed to grow in a humidified 5% CO$_2$ atmosphere in Eagle's basal medium, supplemented with 10% FBS, penicillin (100 units), and streptomycin (100 μg), for 24 hr. Subsequently, the cells were initiated by treatment with 25 μl of the 3-methylcholanthrene (MCA) in acetone stock solution (0.25 mg/ml) to a final concentration of 1 μg/ml of MCA (5 μg/5 ml). The cells were allowed to grow in the presence of the carcinogen or solvent for 24 hr, and the medium in each dish was then replaced with fresh medium containing no carcinogen or solvent. The medium in the dishes was replaced twice per week for the first two weeks of the assay, and thereafter once a week for the remainder four weeks of the assay. In the experiments designed to determine the transformation inhibitory activity of the conjugates, the cells were maintained in the medium containing the conjugates (1 μg/ml) for the first three weeks of the assay; thereafter, the cells were maintained in medium containing no added conjugates.

Six weeks after the carcinogen treatment, the cells were inspected under a microscope for adherence to the culture dishes and were washed with PBS and then fixed in 100% methanol. The fixed monolayers were then stained with Giemsa stain. 20 dishes per group were treated in each experiment. In addition to the test groups, all the transformation assays contained at least three other groups: negative control (not treated with carcinogen or solvent), acetone control (treated with 25 μl of acetone), and positive control [treated with MCA (1 μg/ml) in 25 μl of acetone]. The transformed foci (>3 mm in diameter) in the plates were studied under a microscope and classified according to published guidelines as types I, II, or III [Landolph, J. R. (1985) Transfomatin assay of established cell lines: Mechanism and Application (ed. Kakunaga, T., and Yamasaki, H.) IARC Scientific Publications, Lyon, France pp. 185–201]. Briefly, type III foci were dense, multilayered, basophilic, areas of cell growth which stained to a deep blue color with Giemsa and had rough criss-crossed edges. Type II foci were also dense, multilayered, areas of cell growth, but were stained to a purple color with Giemsa and had smoother, more defined edges compared to Type III foci. Type I foci were not scored in the assay.

The plating efficiency (PE) of the cells was also studied in conjunction with each of the transformation assays. To determine the PE of the cells in the different treatment groups, cells (200 cells/dish) were seeded into three 60-mm petri dishes per experiment group and treated in the identical manner as the transformation assay cells. The cells in these assays were terminated at 10 days, fixed with 100% methanol, and stained with giemsa; the colonies of 50 cells or more visible under a microscope were then counted. The plating efficiency is defined as the (number of colonies/number of cells seeded)*100.

The in vitro anti-transformation activity of BBI, BBIssPal, and BBIssOleic is shown in Table 4. BBI, either as the free protein or in conjugated form to palmitic or oleic acid, was added to the cultures at 1.0 μg/ml for the first three weeks of the transformation assay period starting immediately after the MCA treatment. MCA-treated cells were exposed to 3-methylcholanthrene, dissolved in 25 μl of acetone, at a concentration of 1 μg/ml for 24 hr. Acetone-treated cells were exposed to 25 μl of acetone for 24 hr only. The test groups were exposed to MCA for 24 hr and then to the conjugates for the first three weeks of the assay. Untreated cells were exposed to neither MCA nor acetone. Statistical analysis (Chi-square): Group 4 vs 3, p<0.05; Group 5 vs 3, 0.05<p<0.1; Group 6 vs 3, p<0.05. Control, untreated cells reached confluence in the dishes about 14-days post-seeding formed well adherent, contact-inhibited monolayers. These dishes contained no transformed foci at the end of the assay period. The acetone treated cells also reached confluence and formed well-adhered monolayers 14 days post-seeding and contained no transformed foci. The MCA-treated dishes, however, contained morphologically transformed foci: 6 out of the 19 dishes scored contained type III foci. The BBI-treated group contained no transformed foci, indicating that BBI could prevent MCA-induced transformation in these cells. The BBIssPal-treated cells contained one type II focus out of the 20 dishes scored in the assay. The BBIssOleic treated cells contained no transformed foci. The PE of all the groups in this assay was between 20% to 25%. As demonstrated in Table 4, both BBIssPal and BBIssOleic retained the original biological activity of BBI.

TABLE 4

| Treatment Group | Plating Efficiency (%) | No. of dishes with transformed foci/No. of dishes | Fraction of dishes containing transformed foci |
|---|---|---|---|
| 1. Controls - untreated | 23 ± 1.5 | 0/20 | 0 |
| 2. Negative controls - acetone treated | 22 ± 2.0 | 0/20 | 0 |
| 3. Positive controls - MCA-treated | 21 ± 3.0 | 6/19 | 0.32 |
| 4. Test-MCA treated + BBI | 24 ± 2.0 | 0/20 | 0 |
| 5. Test-MCA-treated + BBIssPal | 23 ± 3.0 | 1/20 | 0.05 |
| 6. Test-MCA-treated + BBIssOleic | 24 ± 3.5 | 0/20 | 0 |

Example 6

Transport of Single- and Multiple-Conjugates

Studies on transport of apical membrane-bound $^{125}$I-BBIssPal were carried out using transwells and six-well plates. In the six-well plate experiments, $^{125}$I-BBI or $^{125}$I-BBIssPal (10 µg/ml) was incubated with Caco-2 cells in serum-free medium for 1 hr at 37° C. Subsequently, the cells were rinsed three times with ice-cold PBS and then divided into two groups. In the first group the internalization of the conjugates was determined after the trypsinization and isolation of the cells. In the second group, the cells were reincubated with serum-free medium and the release of the conjugates from the cells was chased for 24 hr; medium was removed at hourly intervals and counted for radioactivity. At the end of the chase period, the cells were trypsinized, isolated, and counted for accumulated radioactivity. The total counts in each experiments (medium+cell cpms) were determined, and the % of the total counts released at different times was determined.

In the transwell experiments, the conjugates were incubated with the apical side of the cells for 1 hr at 37° C. The transwells were then rinsed three times with ice-cold PBS and then reincubated with serum free medium. The release of the conjugates into the apical and the basal medium was chased for 24 hr by counting the entire basal or the apical medium at different times. The total counts obtained at the end of the chase period (transwells+media counts were added, and the release of the conjugates (% of total) at different times was calculated. To ensure that the counts obtained in the transwells at 24 hr were due to the presence of the conjugates in the cells and not non-specific binding to the plastic, the transwells were exposed to trypsin for 10 min, rinsed three times with ice-cold pbs, and subsequently counted for accumulated radioactivity.

Figure 5A:
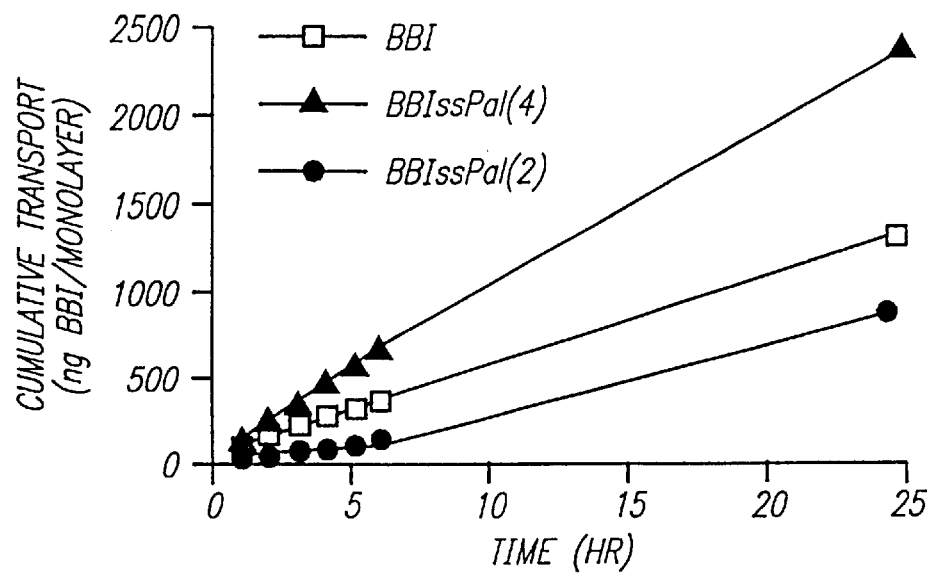
FIG. 5 illustrates transcytosis and accumulation of BBI, BBIssPal(2) and BBIssPal(4) across and into Caco-2 cells.
Figure 5B:
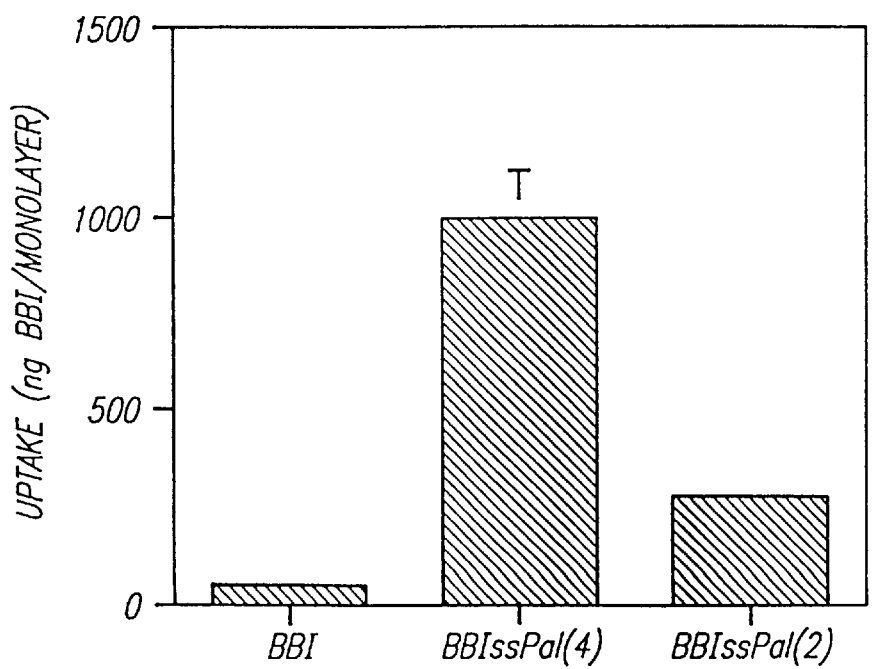
Figure 6:
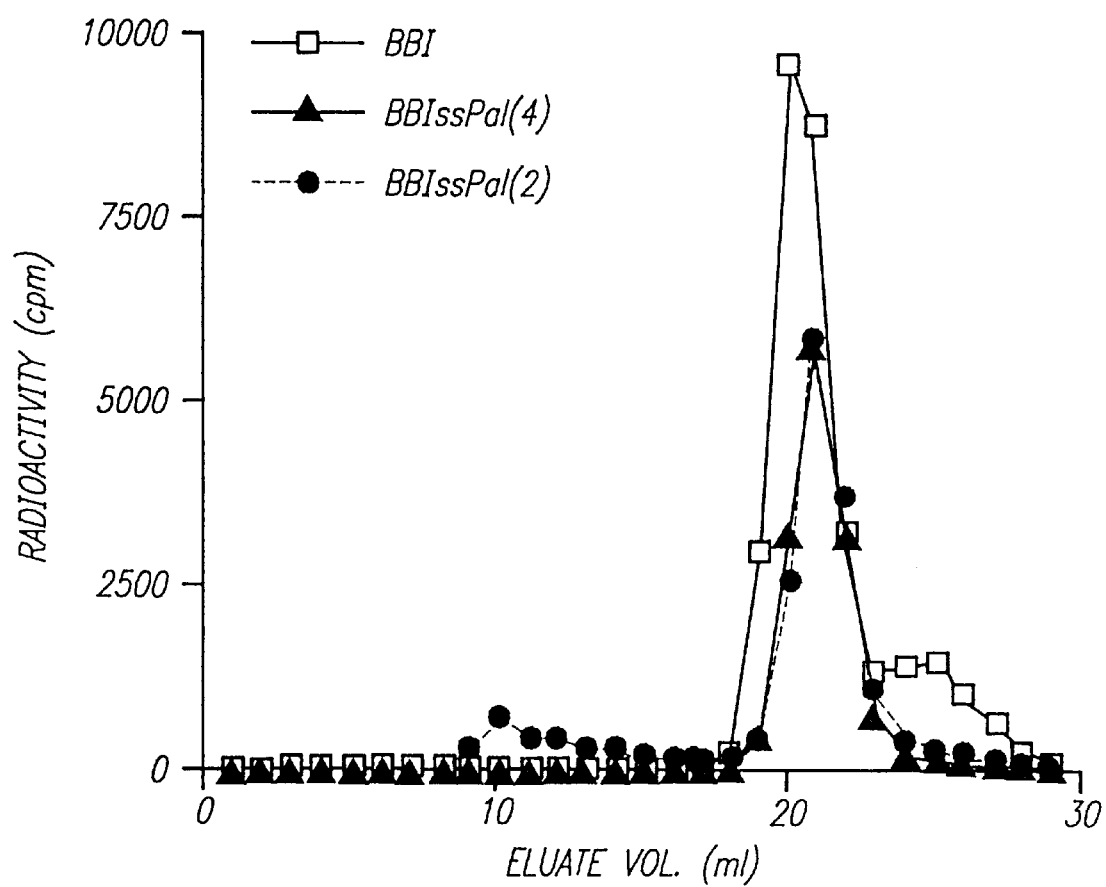
FIG. 6 illustrates the results of G50 gel filtration analysis of basal medium from Caco-2 cells containing transcytosed BBI, BBIssPal(2) and BBIssPal(4).

BBI was modified with 2 or 4 palmitic acids, and the transport was determined in transwells. The cumulative transport of BBI, BBI modified with 4 palmitic acids [BBIssPal(4)], and BBI modified with 2 palmitic acids [BBIssPal(2)] in Caco-2 monolayers is shown in FIG. 5A; the results are expressed as BBI (ng/monolayer)±SEM, n=3. The order of the transport extent was BBIssPal(4) >BBI>BBIssPal(2). The results of the internalization of the conjugates into the same cells is shown in FIG. 5B as the ng of BBI internalized per monolayer. As expected, BBIssPal (4) had the highest uptake into the cells, followed by BBIssPal(2) and BBI. The basal media obtained at 24 hr from the transwells was analyzed using a G50 column; the results are shown in FIG. 6. As had been observed before, neither BBI nor BBIssPal(4) was transcytosed across the monolayers. However, a small, but significant, amount of the basal media of BBIssPal(2) consisted of intact conjugate. This quantity consisted of between about 10 and about 20% of the total radioactivity present in the basal medium.

Example 7

Skin Absorption of BBIssPal

Freshly-prepared skins from hairless mice were mounted on small rings. To each mounted skin, a 5 µl sample of $^{125}$I-labeled BBI or BBIssPal at a concentration of 0.5 mg/ml was applied to an area of 0.38 cm$^2$. Two pieces of skin were used per treatment. The skins were kept at room temperature (23° C.) in a humidified environment. After 30 minutes, the surface of the skins was first rinsed carefully with PBS; subsequently, the skins were unmounted and soaked twice in 100 ml of PBS. The skins were then blotted with filter papers and counted in a gamma counter. The amount of BBI retained on the skins was calculated using the specific radioactivity of the labeled BBI or BBIssPal. The absorption of BBI and BBIssPal into the mouse skins was 0.14 and 1.6 µg/cm$^2$, respectively. This demonstrates that a more than 10-fold increase of BBI absorption into the skin was achieved when the polypeptide was modified using Pal-PDC.

Example 8

Synthesis of Palmitylated Horseradish Peroxidase (HRPssPal)

Ten milligrams of horseradish peroxidase (molecular weight 40,000; Sigma P 8375) in 0.5 ml of PBS was mixed with 2 ml of SPDP in 0.1 ml DMF at 25° C. for two hours. The reaction was terminated by dilution with 0.5 ml PBS, and dialyzed in 500 ml of PBS at 4° C. After 24 hours, the solution in the dialysis tube was removed, reduced by the addition of 50 µl of 1 M DTT, and separated by using a Sephadex G50 column. Fractions at the void volume of the column were pooled and mixed with a 10-fold molar excess of Pal-PDC in borate buffer, pH 9.6 at 25° C. for 4 hours. The reaction mixture was then dialyzed exhaustively at 4° C. for 3 days, and the final product was estimated to contain 10 palmitic acid residues per molecule of HRP. The HRP molecules retained approximately 20% of the original enzyme activity.

Example 9

Cellular Uptake of HRPssPal

Confluent monolayers of mouse fibroblasts L929 cells in 6-well culture cluster plates were incubated in serum-free medium with 30 µg/ml of HRP, either as the native form or as the palmitic acid conjugate (HRPssPal). After 1 hour at 37° C., monolayers were washed three times with PBS and then dissolved in 1 ml of 0.05% of Triton-X100. Cell-associated HRP was determined by measuring the enzymatic activity in each cell extract and the results converted to ng HRP per cell monolayer. Results indicated that cellular uptakes of HRP and HRPssPal were 7 and 229 ng HRP per cell monolayer, respectively. Therefore, a 30-fold increase in cell uptake was achieved by modification of HRP with Pal-PDC.

Example 10

Lipidization of Oligonucleotides

An antisense 21mer oligonucleotide which is complementary to the mRNA of monoamine oxidase B is thiolated using the following procedure. The oligonucleotide is mixed with a two-fold molar excess of cystamine in the presence of a water-soluble carbodiimide reagent, EDC. The mixture is maintained at 25° C. for 2 hours and the a two-fold molar excess to cystamine of DTT is added to reduce disulfide bonds. After separating the oligonucleotide from free cystamine and DTT using a Sephadex G-25 column, a small amount of the thiolated oligonucleotide is reacted with Ellman's reagent and the concentration of sulfhydryl groups determined using the absorbance at 412 nm (assuming an $\epsilon$ of $1.36 \times 10^4$ $M^{-1}$). Subsequently, the number of sulfhydryl groups per oligonucleotide molecule is determined. The thiolated oligonucleotide is mixed in bicarbonate buffer, pH 8, with Pal-PDC in two-fold molar excess to the number of sulfhydryl groups in the oligonucleotide. The palmitylated oligonucleotide is purified using a Sephadex G-25 column.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A compound of general formula V

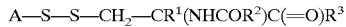

in which A is an aromatic activating residue selected from the group consisting of 2-pyridyl, 4-nitrophenyl and 5-(2-nitro)benzoic acid; $R^1$ is hydrogen, lower alkyl or aryl; $R^2$ is hydrophobic substituent consisting of 4 to 26 carbon atoms, wherein $R^2$ together with the attached carbonyl is a fatty acid acyl group; and $R^3$ is —OH, $R^2$ or an amino acid chain comprising one or 2 amino acids and terminating in —CO$_2$H or —COR$^2$.

2. A compound according to claim 1, wherein $R^1$ is hydrogen $R^2$ is a hydrophobic group and $R^3$ is —OH.

3. A compound of general formula III

in which $R^{3'}$ is —OH or an amino acid chain comprising one or two amino acids and terminating in —CO$_2$H; A is an aromatic activating residue selected from the group consisting of 2-pyridyl, 4-nitrophenyl and 5-(2-nitro)benzoic acid; and $R^1$ is lower alkyl or aryl.

4. A compound according to claim 3, wherein $R^{3'}$ is —OH.

5. A compound according to claim 3, wherein $R^{3'}$ is —NHCH$_2$CO$_2$H.

6. The compound of claim 1, wherein $R^2$ together with the attached carbonyl is palmityl, oleyl or stearyl.

7. A compound of general formula V

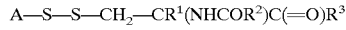

in which A is an aromatic activating residue selected from the group consisting of 2-pyridyl, 4-nitrophenyl and 5-(2-nitro)benzoic acid; $R^1$ is hydrogen, lower alkyl or aryl; $R^2$ is —CH$_2$CH$_2$CH(NH$_2$)CO$_2$H or —CH$_2$CH$_2$CH(NHCOR)COR$^4$; $R^3$ is —NHCH$_2$CO$_2$H or —NHCH$_2$COR$^4$; $R^4$ is a hydrophobic substituent consisting of 4 to 26 carbon atoms, wherein $R^4$ together with the attached carbonyl is a fatty acid acyl group; with the proviso that at least one of $R^2$ and $R^3$ comprises an $R^4$ group.

8. The compound of claim 7, wherein $R^1$ is hydrogen.

9. A compound of general formula V

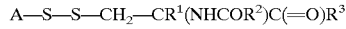

in which A is an aromatic activating residue selected from the group consisting of 2-pyridyl, 4-nitrophenyl and 5-(2-nitro)benzoic acid; $R^1$ is hydrogen, lower alkyl or aryl; $R^2$ together with the attached carbonyl is cholyl or deoxycholyl; and $R^3$ is —OH, $R^2$ or an amino acid chain comprising one or 2 amino acids and terminating in —CO$_2$H or —COR$^2$.

* * * * *

UNITED STATES PATENT AND TRADEMARK OFFICE
CERTIFICATE OF CORRECTION

PATENT NO. : 5,936,092

DATED : August 10, 1999

INVENTORS : Shen et al.

It is certified that an error appears in the above-identified patent and that said Letters Patent is hereby corrected as shown below.

In column 1, after the title and before the paragraph beginning at line 5, please insert the following:

--*Statement Regarding Federally Sponsored Research or Development*

This invention was made with government support under Contract No. UOI-CA 46496, awarded by the National Institutes of Health. The government has certain rights in the invention.--

Signed and Sealed this

Tenth Day of April, 2001

*Attest:*

NICHOLAS P. GODICI

*Attesting Officer*      *Acting Director of the United States Patent and Trademark Office*